(12) United States Patent
Duan et al.

(10) Patent No.: US 10,500,127 B2
(45) Date of Patent: Dec. 10, 2019

(54) VIVO DEVICE AND METHOD OF USING THE SAME

(71) Applicant: Ankon Medical Technologies (Shanghai), LTD., Shanghai (CN)

(72) Inventors: Xiaodong Duan, Pleasanton, CA (US); Junjie Wang, Hangzhou (CN)

(73) Assignee: ANKON MEDICAL TECHNOLOGIES (SHANGHAI) Co., LTD., Shanghai (CN)

( * ) Notice: Subject to any disclaimer, the term of this patent is extended or adjusted under 35 U.S.C. 154(b) by 604 days.

(21) Appl. No.: 15/132,018

(22) Filed: Apr. 18, 2016

(65) Prior Publication Data
US 2017/0296425 A1    Oct. 19, 2017

(51) Int. Cl.
*A61H 23/02* (2006.01)
*A61H 21/00* (2006.01)
*A61F 5/00* (2006.01)

(52) U.S. Cl.
CPC .......... *A61H 21/00* (2013.01); *A61F 5/0073* (2013.01); *A61H 23/02* (2013.01); *A61H 23/0263* (2013.01); *A61H 2201/501* (2013.01); *A61H 2201/5005* (2013.01); *A61H 2201/5007* (2013.01); *A61H 2201/5061* (2013.01); *A61H 2201/5064* (2013.01);
(Continued)

(58) Field of Classification Search
CPC .... A61H 21/00; A61H 23/02; A61H 23/0263; A61H 2201/501; A61H 2230/50; A61H 2201/5061; A61H 2201/5007; A61H 2201/5092; A61H 2201/5064; A61H 2201/5005; A61H 2201/5097; A61H 2201/5084; A61F 5/0013; A61F 5/0073
See application file for complete search history.

(56) References Cited

U.S. PATENT DOCUMENTS 4,239,040 A * 12/1980 Hosoya ................. A61B 10/02
                                                          600/582
9,078,799 B2    7/2015 Shohat et al.
9,155,677 B2   10/2015 Lacy
(Continued)

FOREIGN PATENT DOCUMENTS

AU    2007298473    3/2008
AU    2014224165   10/2014
(Continued)

OTHER PUBLICATIONS

English machine translation for CN 105434155, espacenet.com, translated on Sep. 15, 2018.*

*Primary Examiner* — Tu A Vo
(74) *Attorney, Agent, or Firm* — Treasure IP Group, LLC

(57) ABSTRACT

The vibration capsule device includes a movement generation unit, a movement control unit, a wireless communication unit and a power supply. The movement control unit provides instructions to the movement generation unit, which generates movements in configurable frequencies and duty cycles. The power supply unit provides power to the movement generation unit through movement control unit, which also decides work period and rest period for the capsule device. The vibration capsule device further comprises a capsule movement detection unit, which comprises at least one sensor unit and provides information to the wireless communication unit.

16 Claims, 13 Drawing Sheets

(52) U.S. Cl.
CPC ............... *A61H 2201/5084* (2013.01); *A61H 2201/5092* (2013.01); *A61H 2201/5097* (2013.01); *A61H 2230/50* (2013.01)

(56) References Cited

U.S. PATENT DOCUMENTS

| | | | | |
|---|---|---|---|---|
| 2003/0020810 A1* | 1/2003 | Takizawa | ........... | A61B 1/00105 348/68 |
| 2004/0181155 A1* | 9/2004 | Glukhovsky | ...... | A61B 1/00147 600/476 |
| 2005/0183733 A1* | 8/2005 | Kawano | ............ | A61B 1/00156 128/899 |
| 2006/0169293 A1* | 8/2006 | Yokoi | ................ | A61B 1/00156 128/899 |
| 2007/0123809 A1 | 5/2007 | Weiss | | |
| 2007/0191671 A1* | 8/2007 | Kawano | ............ | A61B 1/00036 600/12 |
| 2007/0229656 A1* | 10/2007 | Khait | ...... | A61B 1/041 348/77 |
| 2007/0238940 A1* | 10/2007 | Amirana | .................. | A61B 5/06 600/302 |
| 2008/0146871 A1* | 6/2008 | Arneson | .............. | A61B 5/0002 600/101 |
| 2008/0281238 A1* | 11/2008 | Oohashi | ............. | A61H 23/0236 601/46 |
| 2009/0274347 A1* | 11/2009 | Gat | .................... | A61B 1/00036 382/128 |
| 2009/0318841 A1* | 12/2009 | Shohat | ................... | A61H 23/02 601/46 |
| 2010/0056963 A1* | 3/2010 | Shaviv | ................... | A61B 17/42 601/46 |
| 2010/0312077 A1* | 12/2010 | Takahashi | .............. | A61B 1/041 600/302 |
| 2011/0017612 A1* | 1/2011 | Dijksman | .............. | A61B 5/073 205/799 |
| 2011/0319727 A1* | 12/2011 | Ishihara | ............. | A61B 1/00016 600/302 |
| 2013/0110017 A1* | 5/2013 | Imboden | ................. | A61H 1/00 601/46 |
| 2014/0378760 A1* | 12/2014 | Ito | .......................... | A61B 5/065 600/103 |
| 2015/0065926 A1* | 3/2015 | Nakamura | ........ | A61B 1/00147 601/46 |
| 2015/0073315 A1* | 3/2015 | Shabbat | ............ | A61B 1/00156 601/46 |
| 2015/0313792 A1 | 11/2015 | Shohat et al. | | |
| 2016/0352185 A1* | 12/2016 | Weiss | .................. | H04M 19/047 |
| 2017/0296092 A1* | 10/2017 | Jones | ..................... | A61B 1/041 |

FOREIGN PATENT DOCUMENTS

| | | | | |
|---|---|---|---|---|
| CN | 201194905 | | 2/2009 | |
| CN | 201211317 | | 3/2009 | |
| CN | 201642791 | | 11/2010 | |
| CN | 1994255 | | 2/2011 | |
| CN | 101984947 | | 3/2011 | |
| CN | 101999976 | | 4/2011 | |
| CN | 1981729 | | 6/2011 | |
| CN | 202060747 | | 12/2011 | |
| CN | 101511305 | | 5/2012 | |
| CN | 103190880 | | 7/2013 | |
| CN | 203437079 | | 2/2014 | |
| CN | 101516314 | | 5/2014 | |
| CN | 104244799 | | 12/2014 | |
| CN | 204655456 | | 9/2015 | |
| CN | 105079970 | | 11/2015 | |
| CN | 105434155 | * | 3/2016 | ............ A61H 23/02 |
| EP | 2073779 | | 7/2009 | |
| EP | 1906830 | | 9/2013 | |
| EP | 2814376 | | 12/2014 | |
| JP | 2011045723 | | 3/2011 | |
| WO | 2008035329 | | 3/2008 | |
| WO | 2013121276 | | 8/2013 | |

* cited by examiner

VIVO DEVICE AND METHOD OF USING THE SAME

CROSS-REFERENCE

None.

TECHNICAL FIELD OF THE DISCLOSURE

This patent application relates to the art of vibration devices for use in medical related applications, and more particularly, to the art of systems and methods of a vibration capsule in in vivo applications.

BACKGROUND OF THE DISCLOSURE

An increasing number of people suffer overweight or constipation. A medical device having a cathartic effect is always used for losing weight or avoiding constipation. If a user uses a drug for a long time, it may lead to a dependency on the drug, and a side effect of dehydration may become an issue for the user. Moreover, a message device in vitro has been developed for losing weight or avoiding constipation. However, the effect of the message device diminishes when there is more internal abdominal fat. Therefore, an in vivo medical device that can safely and effectively to interact with human colonic wall, alleviate colon spasm, promote con motility, treat constipation to enhance the healthy in general is needed.

Vibration capsule by acting on human colonic wall, alleviate colon spasm, promote colonic motility, treatment of constipation, stool discharge, beauty and health. Vibration capsule by acting on the human small intestine wall, promote the small intestine peristalsis, reduce the absorption of the small intestine to the food, achieve weight loss effect. For pseudo obstruction caused by partial small intestine peristalsis, the corresponding segment of small intestine can be stimulated to achieve the purpose of treatment of obstruction.

SUMMARY OF THE INVENTION

The present invention discloses a vibration capsule based in vivo device and the method of using the same.

It is one object of the present invention to provide a vibration capsule that can improve the overall GI tract health for a patient and perhaps lose weight.

It is another object of the present invention that the vibration capsule is very easy to use and a user can have a maximum freedom in managing the capsule when it is placed inside a GI tract of a patient.

It is still another object of the present invention that the vibration capsule can help a patient to achieve the optimal clinical effect without causing any discomfort for a patient.

It is yet another object of the present invention to provide a vibration capsule has long shelf lifetime and long consumer use time.

In one embodiment of the present invention, the vibration capsule device comprises a movement generation unit, a movement control unit, a wireless communication unit and a power supply. The movement control unit provides instructions to the movement generation unit, which generates movements in configurable frequencies and duty cycles. The power supply unit provides power to the movement generation unit through movement control unit, which also decides work period and rest period for the capsule device. The vibration capsule device further comprises a capsule movement detection unit, which comprises at least one sensor unit and provide information to the wireless communication unit.

The sensor unit is selected from an accelerometer (g-sensor), pressure sensor, a temperature sensor, a magnetic field sensor and a gyro sensor.

The power supply unit is selected from Li battery, silver oxide battery, rechargeable battery, and/or a wireless charging unit.

The wireless communication module is selected from a Rf communication method, AC current-magnetic field interactive method, and/or in body contact electrode method.

The movement generation unit is selected from button eccentric motor, linear eccentric motor, magnetic eccentric module. Additionally, the selected motor can be either a single motor or a combination of motors. Each motor can be disposed along a capsule axis, off a capsule axis, in a tilted pasture or any combination of them. In some examples, a gear box is used to increase or reduce speed and torque conversions from a motor to a rotor.

In another embodiment, the vibration capsule device disclosed herein may further comprise a position detection unit, which determines a present or current location of the capsule. The location detection unit comprises a GI tract location detection module and a capsule release indication method. The GI tract location detection module is selected from a time-delay calculation method, a PH-measurement method, a small magnet tracing method, a RF positioning method and an enzyme triggering method. The capsule release indication method comprises a wireless communication method, a temperature sensing method and a magnetic detection method.

In still another embodiment, further comprises a capsule ON/OFF module. The capsule ON/OFF module is selected from Magnetic reed switch, the photosensitive irradiation switch, AC magnetic field sensor switch, RF sensor switch, and a temperature sensor switch.

BRIEF DESCRIPTION OF THE DRAWINGS

Exemplary embodiments of the disclosure will be more clearly understood from the following detailed description taken in conjunction with the accompanying drawings in which.

DETAILED DESCRIPTION OF SELECTED EXAMPLES

Figure 1:
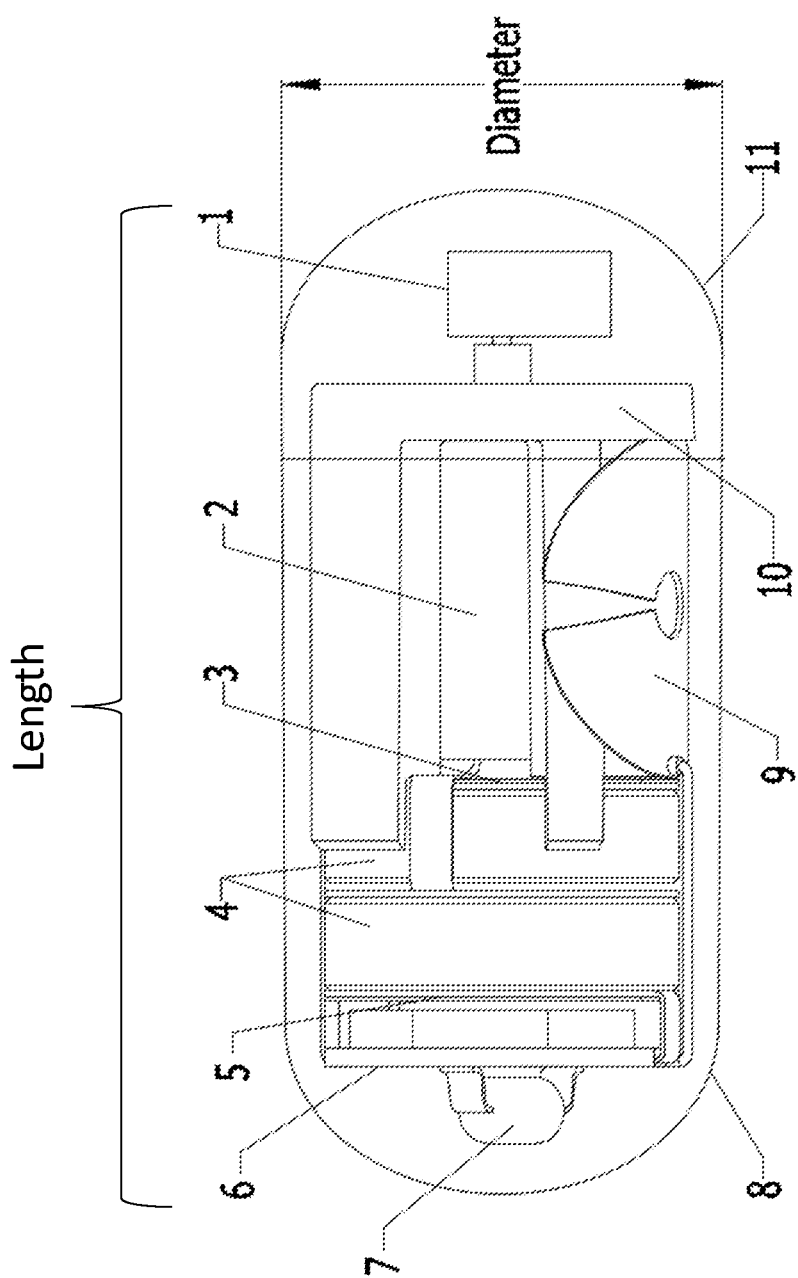
FIG. 1 depicts structural components and their special relationship of an exemplary vibration capsule device in accordance with aspects of the present invention.

Hereinafter, selected examples of a vibration capsule device having first and second movement generators to be placed in a target location and methods of using the same will be described in detail with reference to the accompanying drawings. For simplicity purpose, the vibration capsule device is explained in the context of biomedical applications, i.e. the target location is an in vivo location, for example a location inside a digestive tract. For simplicity purpose, the medical device disclosed herein is designed to be placed in vivo. One of the non-invasive methods of delivery is by swallow into a digestive tract. Therefore the medical device disclose herein is referred as a capsule, which should not be construed as a limitation for its shape, dimension or size. The vibration capsule device disclosed herein and methods of using the same can be implemented for many other applications as long as there is a in situ movement generation means, a control module that can mange the movement generation means and a wireless communication module to communicate with the control module.

It will be appreciated by those skilled in the art that the following discussion is for demonstration purposes, and should not be interpreted as a limitation. Other variances within the scope of this disclosure are also applicable.

The structure and method of using a vibration capsule device is described in detail below. Elements in the drawings are

1 Rotor
2 Motor
3 a second insulation support member
4 power supply unit
5 a first insulation support member
6 PCB
7 Reed switch
8 rear end of the capsule housing
9 RF antenna
10 motor support
11 front end of the capsule housing
21 a vibration motor
24 reed switch
201 a first battery
202 a second battery
231 microprocessor
232 Rf transceiver module
233 one field-effect transistor
234 a RF antenna
300 a magnetic base A vibration capsule system comprises a vibration capsule device, configured to be placed in vivo, and an external operation system including a user interface. In one embodiment, the vibration capsule device is configured to be place inside a patient's GI tract and the external operation system is placed outside of a patient's body. In one example, the external device is portable device such as a smart phone. A basic vibration capsule device, in one embodiment, comprises a vibration generation unit and vibration control unit, together with a wireless communication module, which is configured to communicate with the external operation system through a wireless communication network.

The vibration capsule device disclosed herein comprises capsule functional components and capsule structural components. The capsule functional components include capsule movement generation unit, movement control unit, wireless communication unit, capsule movement detection unit, GI tract location detection unit, power supply unit and power management unit. Further the power management unit comprises a capsule ON/OFF module. The capsule structural components include capsule housing and supporting structures for the functional units.

In a first aspect of the present invention, the vibration capsule device is encapsulated in a housing. The housing is made of high impact resistant material, which ensures that the in situ vibration of the capsule device will not break the housing. The housing is also made of biocompatible materials that will pass safety standard. For example, medical grade of polycarbonate can be used as a capsule housing. In FIG. 1, element 8 and 11 are front end and rear end of a capsule housing.

In accordance with the aspects of the present invention, the capsule can have any shape and geometries. The housing of the capsule device, including but is not limited to diamond, oval, elongated, marquise, dumbbell-shaped and so on. In one example, as shown in FIG. 1, the capsule device comprise is elongated and have two half domed ends. Referring to FIG. 1, the housing for the capsule device have a front end and rear end. In the present invention, the housing of the capsule device has an axis along the length of the capsule device. The power supply unit, movement control unit and movement generation unit are arranged along the axis along the length of the capsule device.

In accordance with the aspects of the present invention, the capsule device can be of any dimension or size as long as the vibration capsule device can be placed in vivo. For example, it is preferred that a vibration capsule device can be introduced into a patient GI tract in a non-invasive method such as swallowing. The patient herein includes both human being and an animal. Referring to FIG. 1, the capsule device has a length from its front end to its rear end. In one example, the length of the capsule device is 27.6 mm. Also referring to FIG. 1, the capsule device has two half-domed ends. The diameter for the half dome ends is the diameter of the capsule device. In one example, the diameter for the capsule device is about 11.8 mm.

In accordance with the aspects of the present invention capsule device can be of any weight as long as it does not cause significant discomfort for the patient when it moves or vibrates. The weight is distributed along and around the capsule axis. As shown in FIG. 1, the power supply unit, movement control unit and movement generation unit are arranged along the axis along the length of the capsule device. In one example, the weight of the capsule is less than 6 g. In another example, the weight of the capsule is less than 5 g. In still another example, the weight of the capsule is less than 4.5 g. Further, the vibration capsule device disclosed herein, is configured to generate either a stirring or vibration motion to massage the GI tract wall to improve the in vivo digestive conditions. The weight of the vibration capsule devices is proportional related to the effectiveness of the massages. In one example, the weight of the capsule is more than 2 g. In another example, the weight of the capsule is less than 3 g. In still another example, the weight of the capsule is less than 4 g. In still another example, the weight of the capsule is more than 4.5 g.

In a second aspect of the present invention, the vibration capsule device comprises a capsule movement generation unit and capsule movement control unit. The movement generation unit provides in situ force to produce the vibration of the capsule. The movement generation unit is selected from button eccentric motor, linear eccentric motor, magnetic eccentric module. Additionally, the selected motor can be either a single motor or a combination of motors. Each motor can be disposed along a capsule axis, off a capsule axis, in a tilted pasture or any combination of them. When the capsule device vibrates, in one example, the vibration direction is perpendicular to the axis of the capsule device. When the capsule device vibrates, in another example, the vibration direction is neither parallel nor perpendicular to the axis of the capsule device, but forming an angle between 0-90°. Referring to FIG. 1, a capsule axis is along its length direction from the front to the back. If the capsule adopts an orientation as shown in FIG. 1 then the vibration direction is perpendicular to the capsule axis means the vibration direction is along up and down direction. In some examples, a gear box is used to increase or reduce speed and torque conversions from a motor to a rotor.

Figure 2:
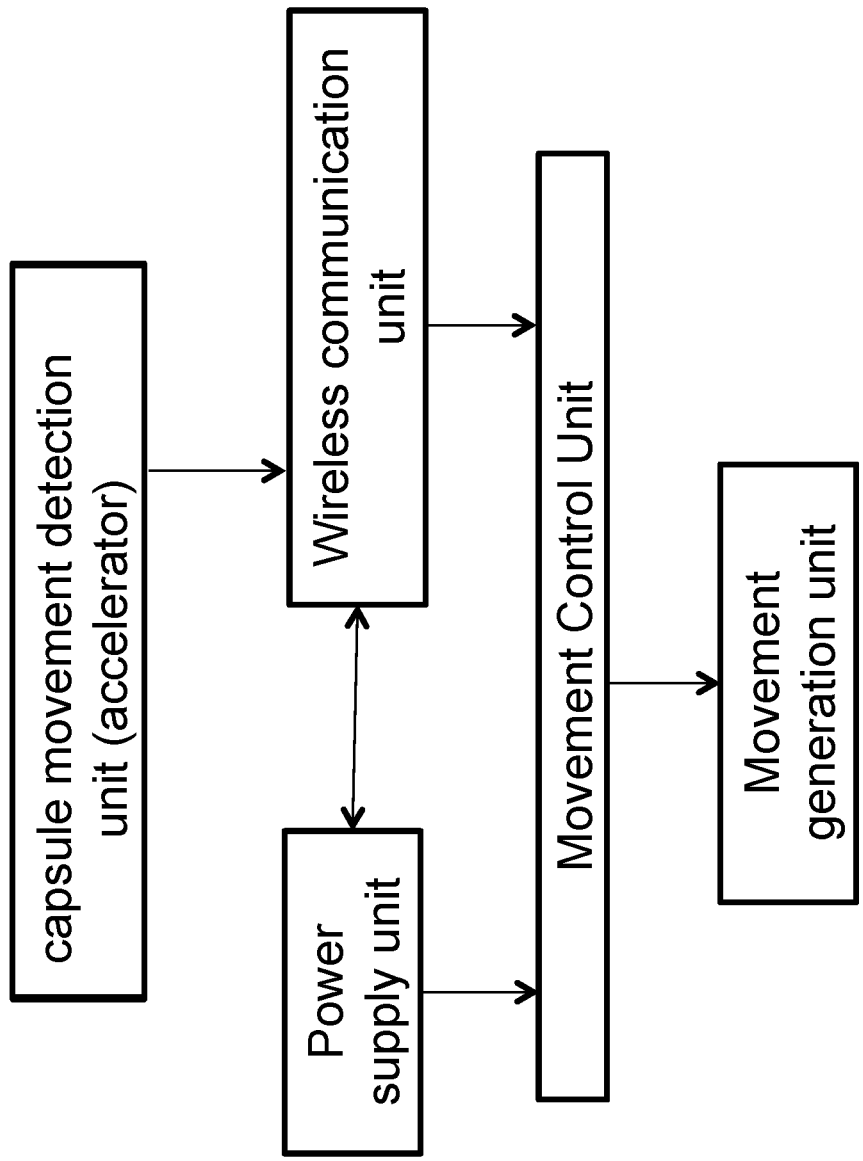
FIG. 2 diagrammatically illustrates functional units of another exemplary vibration capsule device in accordance with aspects of the present invention.

In one embodiment, the movement generation unit, in the present invention, comprises a first movement generator and a second movement generator. In one example, the first movement generator is a motor element and the second movement generator is a rotor element. In FIG. 1, element 2 is a motor element and element 1 is a rotor element. The motor element provides a forced vibration to the vibration capsule device. Referring to FIG. 2, the movement generation unit is capable of taking control signals from other units internally or externally, to generate operable movement control instructions and send the same to the capsule movement generation unit. The instruction includes and is not limited to a periodic and steady-state input, a transient input, or a random input to deliver either a harmonic or a non-harmonic vibration. The vibration of the capsule device in the present invention has a controllable protocol having an alternating work period and rest period, which is managed by a power supply or together with a power supply management unit. The vibration of the capsule device in the present invention has an adjustable frequency and/or duty cycle, which is controllable from a movement control unit. The movement generation unit can generate vibration having a frequency between 1-20 Hz, the duty cycle is adjustable between 0.01 to 0.9.

By adjusting the relative ratio between active (on) and inactive (oft) state, the vibration level or strength is adjusted. For example in a strong or high vibration level, the frequency is from 15-20 Hz. In one example, with one duty cycle, the ratio between ON state to OFF state is 1:1 to 1:2. In a weak or low vibration level, the frequency is from 4 Hz to 6 Hz. In one example, with one duty cycle, the ratio between ON state to OFF state is 1:3 to 1:5.

The capsule movement control unit sends operable instructions to the movement generation unit. In one embodiment, the capsule movement control unit change individual parameters such as motor rotation speed, on/off frequency (referring to FIG. 6), on/off duty cycle, time duration or ratio between work period and rest period in each cycle directly. In another embodiment, the capsule movement control unit does not change individual parameters. Instead, the capsule movement control unit changes between vibration levels as well as directions, wherein each level has a pre-determined portfolio of parameters motor rotation speed, on/off frequency (referring to FIG. 6), on/off duty cycle, time duration or ratio between work period and rest period in each cycle. The different vibration levels have at least one parameters is different from that of the other. The different vibration levels can progressively increase or progressively decrease. The different vibration levels of the vibration capsule device can be either continuous levels or discrete levels. In one embodiment, the capsule movement control unit is configured to at least adjust the vibration levels of the capsule device between a first and second thresholds, wherein the first threshold is a maximum vibration level that a patient feels comfortable; and the second threshold is a maximum vibration level that the same patient can endure without any other side effect. Further, the capsule movement control unit can adjust the vibration from inactive state to active state either continuously or at discrete intermediate levels, either from turn ON of the capsule device or change from a rest period to work period.

The vibration magnitude of the capsule device in the present invention has a customized value, which is predetermined after the manufacture process. Each vibration capsule device can be customized made to have different vibration magnitude. In one embodiment of the present invention, the motor element is an eccentric motor. In one embodiment of the present invention, the rotor element 1 can be made of magnetic element, so that magnetic tracing can be used as one of the location detection method. In another embodiment of the present invention, the motor element can rotate between 100 cycles/min and 10000 cycles/min.

In a third aspect of the present invention, referring to FIG. 2, the vibration capsule device comprises a powers supply unit. In one embodiment, the movement control unit is electrically connected to the power supply unit. The power supply unit is selected from Li battery, silver oxide battery, rechargeable battery, and/or a wireless charging unit. The power supply unit provides power to all the units, including wireless communication unit, movement control unit and capsule movement detection unit. Further, the power supply unit may optionally connect to a power management unit to optimize the power supply to all the units and conserve power, improve the operation lifetime of the vibration capsule device. In FIG. 1, element 4 are batteries as power supply unit. In one example, the power management unit is configured as part of the PCB to connect between power supply unit and movement control unit.

In one embodiment, power supply unit provides power to all the capsule functional units in the vibration capsule device through a power management unit. In one example, the power management unit comprises a capsule ON/OFF module, which adjusts the capsule to be in a work period or a rest period according to a timing protocol. For example, referring to FIG. 4, the power management unit includes a timing unit, the vibration capsule device has an alternating working and rest state.

In a fourth aspect of the present invention, the vibration capsule device comprises a wireless communication unit. The wireless communication module can be selected from a Rf communication method, AC current-magnetic field interactive method, and/or in body contact electrode method. In one embodiment, referring to FIG. 1, wireless communication unit includes Rf antennas, a Rf transceiver module and a PCB unit. Through the wireless communication unit, the vibration capsule device can establish a connection with a Bluetooth device, which in turn communicates with an external device for example smart phone or Internet data center or a cloud server center. The Rf transceiver can use either 433 MHz, or 2.4 GHz as communication frequency.

In one embodiment the wireless communication module receives information from a capsule movement detection unit and send the capsule movement detection data to the external device, the external device will perform analysis and send instructions back to the wireless communication unit. Then wireless communication unit will turn the instruction received from external device, into data receivable by the movement control unit. In alternative embodiment, the data received from the capsule movement detection unit will be calculated and analyzed before sending out to the external device. The external device further comprises a user interface that allows a patient to examine the basic capsule characteristic and manually input or adjust capsule vibration levels. The basic capsule characteristic includes a capsule serial number, current vibration frequency, duty cycle, work period rest period, manufacture date, capsule turn-on time etc.

In another embodiment, the wireless communication module also receives information from a GI location detection unit, which collect data in order to identify the current location of the capsule device. In one example, the data about the current location is first sent to the external device through wireless communication unit. In an alternative example, data about the current location is analyzed by a processor, or compared with a previous data stored in a memory before getting sent out to the external device. After the external device received the information, an instruction directing to the movement control unit will be sent again to the wireless communication module. By doing so, the vibration level can be adjusted to different levels through live communication between the movement control unit and external device through wireless communication unit.

In one embodiment, the external device is a smart phone, which further connected to a network with a data center or cloud service center. The external device is a user specific device that can retrieve specific individual capsule identification information from the wireless communication unit. The capsule identification information includes a data of manufacture, suitable vibration strength, vibration magnitude, weight and size, etc. The external device can also retrieve user specific, and/or GI tract location specific information such as past/previous tolerance level data as well as data relevant statistical or average data for similar user scenarios, or similar demographic group of patients, or for treatment of similar stages of disease symptoms.

In a fourth aspect of the present invention, the vibration capsule device further comprises a capsule movement detection unit. In one embodiment, the vibration detection unit is a patient's own GI tract, which can sense a difference between high or low level of the vibration and provide feedback to increase or decrease the vibration level. In this embodiment, once the vibration capsule is turned on, the intended vibration levels can be adjusted qualitatively. A patient's previous threshold level can be stored and retrievable every time when a capsule is turned on. Real time feedback can be used to adjust desired vibration levels through the user interface in qualitative manner.

However, preferably, the actual vibration level of the capsule device in active state should be detected and monitored in real time in a more scientific and quantitative manner, for both safety and therapeutic purposes.

The purpose of the vibration detection unit is to monitor and measure the actual level of vibration and provide feedback to a patient, so that a patient or a user can use external device to adjust and optimize the vibration value in real time. By doing so, even though the capsule device may not be customized but the vibration level for different patient can be individualized or personalized for different patient. Further even for the same patient, the vibration level at different time, or at different GI location, or for different purpose can be adjusted accordingly. For example, the vibration level can start out weak and gradually increase as treatment going from early phases to later phases in a very systematic manner.

The capsule movement detection unit employs the basic principle that when the capsule device vibrates, the generated vibration related parameters at different parts of the capsule device are different. When the capsule device vibrates, different parts of the capsule device interact with the GI wall differently, thus different parts of the capsule device receive different acceleration, pressure, temperature, and ground magnetic field. Detecting at least one of these parameters in real time for different parts of the capsule device will provide very useful and reliable vibration profile in real time to a patient through wireless communication unit.

A sensor device is disposed on at least one part of the vibration capsule device, can detect the vibration related parameter. The sensor device can be selected from an accelerometer (g-sensor), pressure sensor, a temperature sensor, a magnetic field sensor and a gyro sensor, or a combination of them. One or more sensor devices can be placed on the outside of the vibration capsule device. In one example, one sensor device is placed next to the rotor. In another example, one sensor device is placed next to the motor on the side. In another example, there are two sensor devices present in the vibration capsule device, one on each end of the vibration capsule device, because the two ends of the capsule is expected to have the most difference in its vibration related parameters.

The sensor device is used to detect and monitor vibration of the movement generation unit. In one example, the sensor device is turned on automatically as soon as the vibration capsule device is turned on. In another example, the sensor device is turned on to monitor vibration when it receives an external instruction sent from the user interface of the external device. In still another example, the sensor device is turned on when it arrives at certain location, wherein the location information is collected and analyzed through GI tract location detection unit. In still another example, the sensor device is turned on after a specific time s after the capsule device is turned on. For example, the capsule device is turned on as soon as it is swallowed then the accelerometer is turned on basic an estimated time of arrival at a target location after time s. The turned on and off of the capsule movement detection unit can be managed by the power management module.

After the vibration related parameters are collected by the sensor device, the data may be sent as crude data to the external device and wait for further instructions. Alternatively, the crude data of the vibration related parameters may be processed or manipulated, either preliminarily or extensively before being sent out to the external device. In a first embodiment, the vibration related parameters are collected within a first time duration to form a first group of data collection, an average value of the first group of data is calculated and taken to represent the current vibration data for the first time duration. Subsequently, the current vibration data for the first time duration is sent out through the wireless communication unit to the external device. In a second embodiment, the vibration related parameters are collected within a second time duration to form a second group of data collection, a median value of the second group of data is calculated and taken to represent the current vibration data for the second time duration. Subsequently, the current vibration data for the second time duration is sent out through the wireless communication unit to the external device. In a third embodiment, the vibration related parameters are collected within a third time duration to form a third group of data collection, a maximum value of the third group of data is calculated and taken to represent the current vibration data for the third time duration. Subsequently, the current vibration data for the third time duration is sent out through the wireless communication unit to the external device. Based on the current vibration data received by the external device, the external device will send out instruction to increase the vibration level, decrease the vibration level or keep the same vibration level.

In accordance with the aspects of the present invention, the vibration level is determined by a combination of parameters including motor rotation speed, on/off frequency (referring to FIG. 6), on/off duty cycle, ratio between work period and rest period in each cycle. A change in any one of the above parameters will affect the vibration level of the vibration device.

In a first embodiment of the fourth aspect of the present invention, a sensor device is an accelerometer. The accelerometer is used to detect and monitor vibration of the movement generation unit. The information detected by the accelerometer will be first collected be analyzed to be used to make adjustment to vibration of the capsule device. The accelerometer measures proper acceleration ("g-force") of the vibration capsule device.

In one example, the capsule is cylinder shaped having two half-domed ends, as shown in FIG. 1. Two accelerometers are present in the capsule device. Two accelerometers are attached to both ends of the capsule device. When the capsule device vibrates, the accelerator on the front and back end of the capsule device, detecting the acceleration data of the front and back end of the capsule device. Once the acceleration data is collected, an average between the two is calculated and the average value of the two acceleration data is sent to the external device through the wireless communication unit and wait for the instruction for next step.

In a second embodiment of the fourth aspect of the present invention, a sensor device is a pressure sensor. Because when a capsule device vibrates, different part of the capsule device receives different pressure from the GI tract, therefore monitor a pressure changes in the vibration capsule can provide quantitative feedback regarding the vibration level.

In one example, the capsule is cylinder shaped having two half-domed ends, as shown in FIG. 1. Two pressure sensors are present in the capsule device. Two pressure sensors are attached to both ends of the capsule device. When the capsule device vibrates, the pressure sensor on the front and back end of the capsule device, detecting the pressure data of the front and back end of the capsule device. Once the pressure data is collected, a greater value between the two is calculated and the greater value of the two pressure data is sent to the external device through the wireless communication unit and wait for the instruction for next step.

In a third embodiment of the fourth aspect of the present invention, a sensor device is a temperature sensor. Because when a capsule device vibrates, some part of the capsule device may contact with a patient's GI tract wall while another part of the capsule device may not contact with a patient's GI tract wall, thus different temperature may be generated during the vibration. Therefore, monitoring a temperature changes in the vibration capsule can provide quantitative feedback regarding the vibration level.

In one example, the capsule is cylinder shaped having two half-domed ends, as shown in FIG. 1. Two pressure sensors are present in the capsule device. Two temperature sensors are attached to both ends of the capsule device. When the capsule device vibrates, the temperature sensor on the front and back end of the capsule device, detecting the temperature data of the front and back end of the capsule device. Once the temperature data is collected, a greater value between the two is calculated and the greater value of the two temperature data is sent to the external device through the wireless communication unit and wait for the instruction for next step.

In a fourth embodiment of the fourth aspect of the present invention, a sensor device is a magnetic field sensor. Because when a capsule device vibrates, different part of the capsule device interacts with the ground magnetic field differently, therefore monitoring a sensed magnetic field change in the vibration capsule can provide quantitative feedback regarding the vibration level.

In one example, one magnetic field sensor is present in the capsule device. The magnetic field sensor is attached to capsule housing in close proximity to the motor. When the capsule device vibrates, the magnetic field sensor, detects the ground magnetic field influenced magnetic field data of the capsule device. Once the sensed magnetic field data is collected, the data is sent to the external device through the wireless communication unit and wait for the instruction for next step.

In a fifth embodiment of the fourth aspect of the present invention, a sensor device is a gyro sensor. Because when a capsule device vibrates, different part of the capsule device experiences different angular velocity applied to the vibration capsule device, therefore monitoring a angular velocity change in the vibration capsule can provide quantitative feedback regarding the vibration level.

In one example, one gyro sensor is present in the capsule device. The magnetic field sensor is attached to capsule housing in close proximity to the motor. Once the data is collected by the gyro sensor, the data is sent to the external device through the wireless communication unit and wait for the instruction for next step.

The use of one or multiple sensors can help to identify an optimal vibration frequency, duty cycle and rest period for each individual patient Based on the information received by the external device, a library of the related frequency, duty cycle and rest period can be built and associate with the library with a vibration level identification.

Once the vibration level has been accurately feedback to the external device, external device can trace the vibration level information and corresponding relevant environment information together, and stored in a memory in external device. Every time, the capsule device either wake up from a rest period or is restarted, the previous vibration level information can be retrieved easily from the storage.

Optionally, the sensor device used to detect and monitor vibration of the movement generation unit is calibrated before deployment in a patient. In one example, a default vibration level including motor rotation speed, frequency and duty cycle is stored in each vibration capsule. A default or start out vibration run and sensor detection is performed before the capsule is introduced in vivo. During the default run, a calibration protocol is performed to include noise levels corresponding to relevant sensor device at use.

In a fifth aspect of the present invention, the vibration capsule device further comprises a GI tract location detection unit. The GI tract location detection unit comprises a position detection unit and capsule release indication unit. The GI tract position detection units detect current position of the vibration capsule device, in one embodiment, the current position information is sent to external device through the wireless communication unit. In another embodiment, the current position information is sent to the power management module to decide if on or off information should be sent to the movement control unit. The method to detect the current position of the vibration capsule device include and is not limited to, a time-delay calculation method, a PH-measurement method, a small magnet tracing method, a RF positioning method and an enzyme triggering method. The capsule release indication method comprises a wireless communication method, a temperature sensing method and a magnetic detection method.

In a first embodiment of the fifth aspect of the present invention, the position detection unit uses a time-delay calculation method, and wherein the position detection unit is a timer and data sending and receiving element. The time-delay calculation method includes a timing protocol to predict if the vibration capsule has arrived in colon based on a timing element. In one example, timing element is a pre-determined value, comparing how long the capsule has traveled inside a patient's GI tract with the pre-determined value, a decision is made if the vibration capsule has arrived in colon or not. The pre-determined value can be an average data for certain group of people similar to the patient. The pre-determined value can also be a previous data for this patient during a previous vibration capsule procedure.

In a second embodiment of the fifth aspect of the present invention, the position detection unit uses a PH-measurement method, and wherein the position detection unit is a PH sensor. The colon neighboring areas have P values around 7.8. The PH sensor can accurately detect PH values from 2-12. In one example, the PH sensor can detect PH values from 4-8. In another example, the PH sensor can detect PH values so that it can tell if the PH value is 7.6-8 or not.

In a third embodiment of the fifth aspect of the present invention, the position detection unit uses magnetic field tracing method, and wherein the position detection unit is a small magnetic dipole element. The small magnetic dipole element has a magnetic dipole moment from 0.1 $Acm^{-2}$ to 1 $Acm^{-2}$ and a weight about 0.5 g-5 g. The travel of the vibration capsule device is traced in to a map according to the movement of the magnetic dipole element. Based on the tracing map, the current position of the vibration capsule is determined.

In a fourth embodiment of the fifth aspect of the present invention, the position detection unit uses surface magnetic, RF or ultrasonic sensing method, and wherein the position detection unit is an external sensing unit placed near ileocecal valve of the patient. By doing so, once the vibration capsule enters into the colon, a signal is detected by the external sensing unit.

In a fifth embodiment of the fifth aspect of the present invention, the position detection unit uses enzyme-triggering method, and wherein the position detection unit is enzyme sensor placed on the exterior of the vibration capsule device. The enzyme sensor is configured to specifically detect if a colon enzyme is present. If the colon enzyme is present, the enzyme sensor will send a signal to either the external device or to the power management unit.

In another aspect of the present invention, the position detection unit uses a plurality of magnetic, RF, or ultrasonic sensors positioning method, and wherein the position detection unit is a plurality of magnetic, RF, or ultrasonic sensors placed on a patience body along the propagation direction of the patient's intestine. When the vibration capsule travels at colon, the closest sensor shall detect a strongest signal, so the location of the vibrating capsule can be detected along the colon.

In a sixth embodiment of the fifth aspect of the present invention, the capsule release indication unit uses a wireless communication method, wherein the capsule release indication unit is part of the wireless communication unit. In one example, the capsule sends out the signals to the outside periodically. Once the signal received is outside a certain pre-determined circle, then it can be decided that the capsule is no longer in the patient.

In a seventh embodiment of the fifth aspect of the present invention, the capsule release indication unit uses temperature based method, wherein the capsule release indication unit is a temperature sensor disposed on the exterior of the vibration capsule device. When the vibration capsule device is inside a patient, the temperature sensor senses in body temperature at about 36 degrees and whereas the vibration capsule device is released to the environment, the temperature sensor detects an environment temperature which is different from the in body temperature. In one example, the temperature sensor detects the temperature where the capsule device is in periodically, send the information to appropriate devices to signal if the capsule has been released or not.

In an eighth embodiment of the fifth aspect of the present invention, the capsule release indication unit uses a magnetic field based detection method, wherein the capsule release indication unit is a small magnet having a permanent magnetic dipole disposed on the inside of the vibration capsule device. The movement of the small magnet is tracked periodically. A map of the position of the small magnet can be generated to indicate its current position to decide if the vibration capsule has been released.

In a sixth aspect of the present invention, the vibration capsule device further comprises a capsule ON/OFF module. The capsule ON/OFF module is configured to turn the overall capsule to active or inactive state to minimize overall power consumption and improve the lifetime especially the shelf life of the vibration capsule. In one embodiment, the vibration capsule is turned on when it is taken out of the package and ready to be deployed. In another embodiment, the vibration capsule is turned on when it arrives in a target specific position, for example the colon of a patient. In one example, the capsule ON/OFF module is a standalone module. In another example, the capsule ON/OFF module is part of power management unit. In still another embodiment, capsule ON/OFF module is a combination of a part of power consumption module and standalone module for example, a packaging of the vibration capsule device. The capsule ON/OFF module is selected from a magnetic reed switch, the photosensitive irradiation switch, AC magnetic field sensor switch, RF sensor switch, and a temperature sensor switch.

Figure 13:
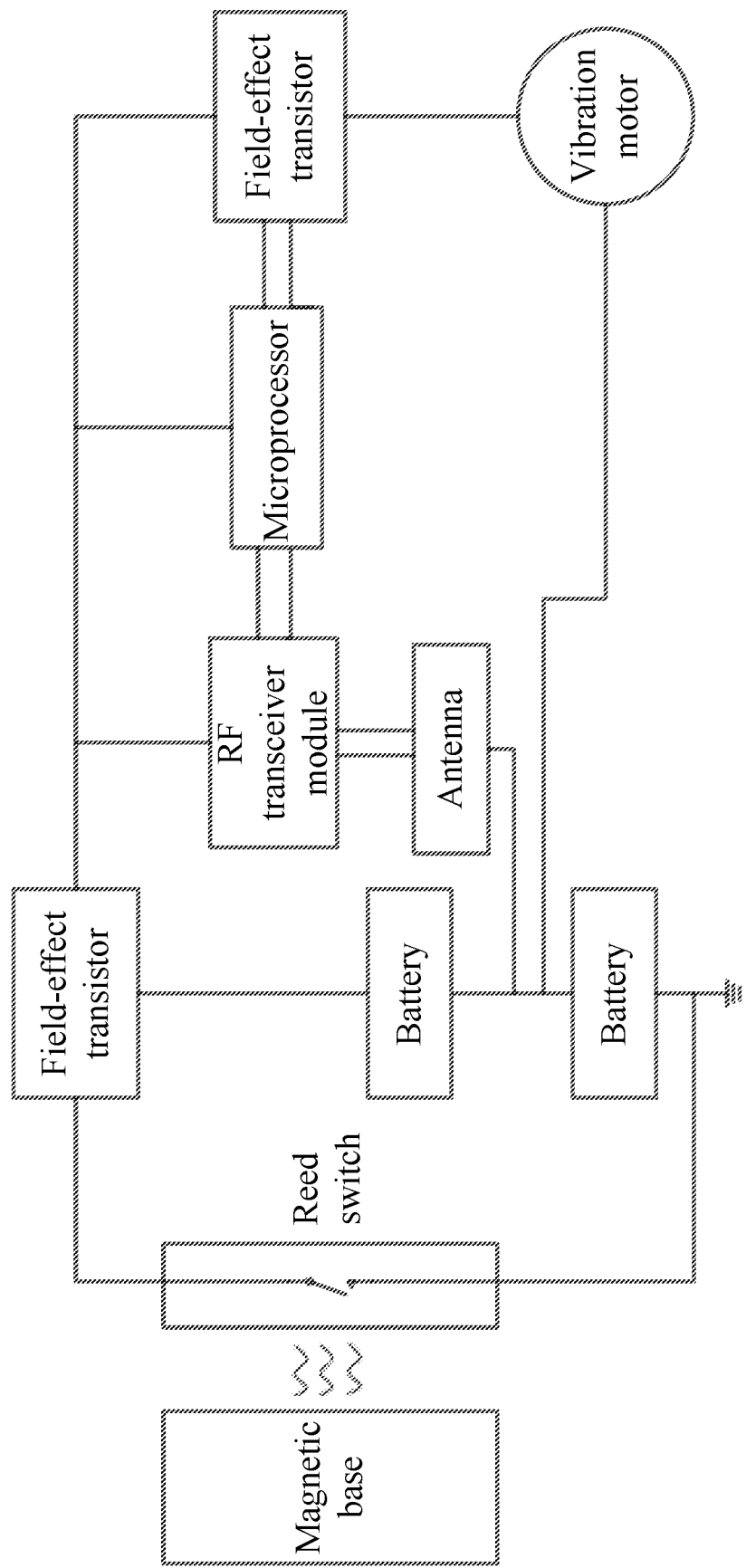
FIG. 13 is a schematic diagram of an exemplar control circuit of the present invention.

In a first embodiment of the sixth aspect of the present invention, the capsule ON/OFF module is a Magnetic based reed switch. In one example, the vibration capsule is placed inside a magnetic packaging. When the capsule is inside the packaging the vibration capsule is OFF. Once the packaging is removed, the capsule is turned ON by the reed switch. Referring to FIG. 13, a magnetic reed switch 24 is used in a control circuit for the vibration capsule device. The magnetic reed switch 23 works with the magnetic base 300, which is included in a packaging of the vibration capsule device, a magnetic pair. When the magnetic base 300 is placed in proximity of the reed switch 24, the reed switch is an OFF state and control circuit is open. When the magnetic base 300 is removed away from the reed switch 24, the reed switch is in a ON state, connecting to the control circuit.

In a second embodiment of the sixth aspect of the present invention, the capsule ON/OFF module is a light sensitive switch or photo-radiation switch. In one example, the vibration capsule is placed inside a dark packaging, not exposed to light. When the capsule is inside the packaging the vibration capsule is in its OFF state. When the capsule device is taken out of the packaging, as soon as the capsule is exposed to light, the vibration capsule device is turned on. The light sensitive switch can be controlled by a certain wavelength of the light or certain color of the light.

In a third embodiment of the sixth aspect of the present invention, the capsule ON/OFF module is an AC magnetic field-sensitive switch. An external magnetic field can be used to turn On and OFF the capsule device.

In a fourth embodiment of the sixth aspect of the present invention, the capsule ON/OFF module is a radio frequency sensitive switch. The vibration capsule device can be turned ON and OFF remotely by using radio frequency.

In a fifth embodiment of the sixth aspect of the present invention, the capsule ON/OFF module is a temperature sensitive switch. The vibration capsule device is turned ON/OFF based on the temperature that the sensor detects. When the vibration capsule is placed inside an in vivo device, the temperature sensor senses a surrounding temperature of 36, and the vibration capsule device is turned on. When the vibration capsule is released to the environment, the temperature sensor senses a surrounding temperature of 20, and the vibration capsule device is turned OFF.

In a seventh aspect of the present invention, a control circuit of the vibration capsule device can be used to adjust the vibration direction of the capsule device. An exemplar control circuit for the vibration capsule device in accordance with the aspects of the present invention is shown in FIG. 13. In one embodiment of the present invention, power supply, which is the battery 201 and 201 supplies power to the vibration motor 21, wherein two field-effect transistors 233 bridges the electrical communication between the power supply unit and vibration motor 21. The field-effect transistors 233 turn on and off the electric current to the vibration motor 21 from the power supply unit. Furthermore, the flow direction of the current can be adjusted through the two field-effect transistors that the electric current from the batteries can be flowed in either a forward direction or in a backward direction; correspondingly the vibration direction of the vibration motor can be adjusted. For example, if the vibration motor receives electrical current in a forward direction, the motor vibration moves in a clockwise direction, whereas the vibration motor receives electrical current in a backward direction, the motor vibration moves in a counter-clockwise direction.

Referring to FIG. 1, rotor element 1 and motor element 2 together with a connecting axis form the capsule movement generation unit. Battery element 4 can be a series of batteries, which is the power supply unit. PCB board 6 provides the essential board to host the power management unit, movement control unit, and a processor of the capsule detection unit and a processor for the capsule GI tract location unit. Reed switch 7 belongs to the capsule ON/OFF module. RF antenna 9 is part of the capsule wireless communication module. The first insulation support member 5, the second insulation support member 3 and motor support provide important structural support for the capsule device. The rear end of the capsule housing 8 and front end of the capsule housing 11 form important capsule protective housing.

Figure 9:
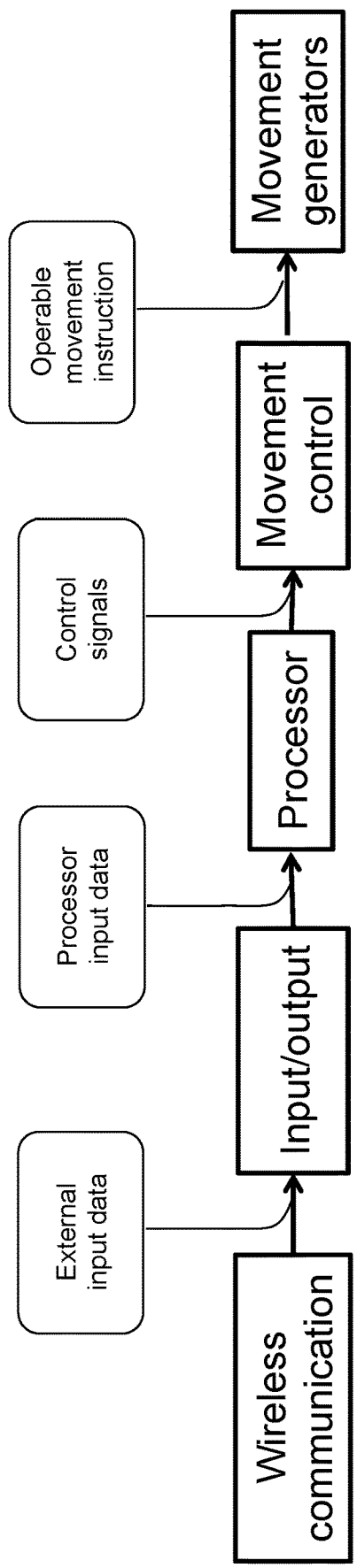
FIG. 9 shows in one embodiment how an instruction flows from a wireless communication unit to the movement generation unit.

FIG. 2 shows one embodiment of the vibration capsule device. The vibration capsule device comprises a movement generation unit, capable to generate vibration movement, characterized by a frequency between 1-10 Hz, duty cycle between 0.01 to 0.9; a movement control unit, configured to receive movement control signals from a wireless communication unit and send operable movement control instructions to the movement generation unit; and a power supply unit, providing power to the vibration capsule device, wherein the wireless communication unit comprises a RF transceiver and communicate data to an external device and receive instruction from the external device. Further the vibration capsule device comprises a capsule movement detection unit, which detects the vibration related parameters and sends to wireless communication unit. Referring to FIG. 9, the wireless communication unit is capable to receive external instruction data from the external device, and send the instruction through a input/output unit to processor, the processor converts processor input data to control signals and send to the movement control unit, then the movement control unit send operable movement instruction to movement generation unit.

Figure 3:
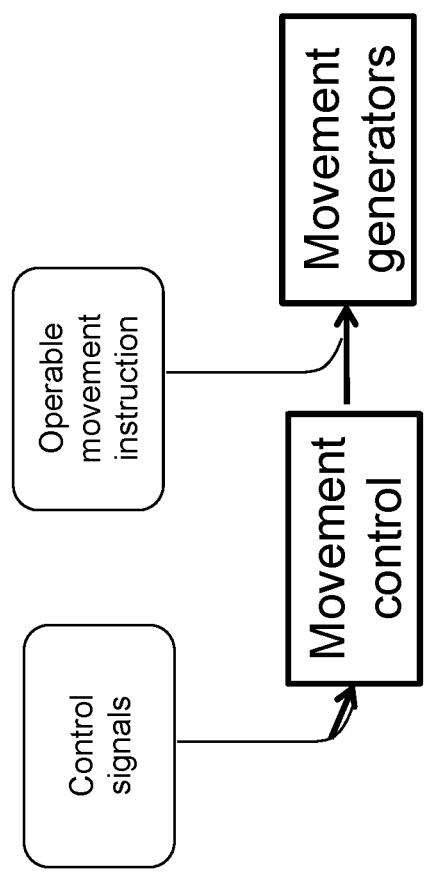
FIG. 3 diagrammatically illustrates movement control unit and movement generators of another vibration capsule device in accordance with aspects of the present invention FIG. 4 diagrammatically illustrates functional units of another exemplary vibration capsule device having a power management unit in accordance with aspects of the present invention.
Figure 6:
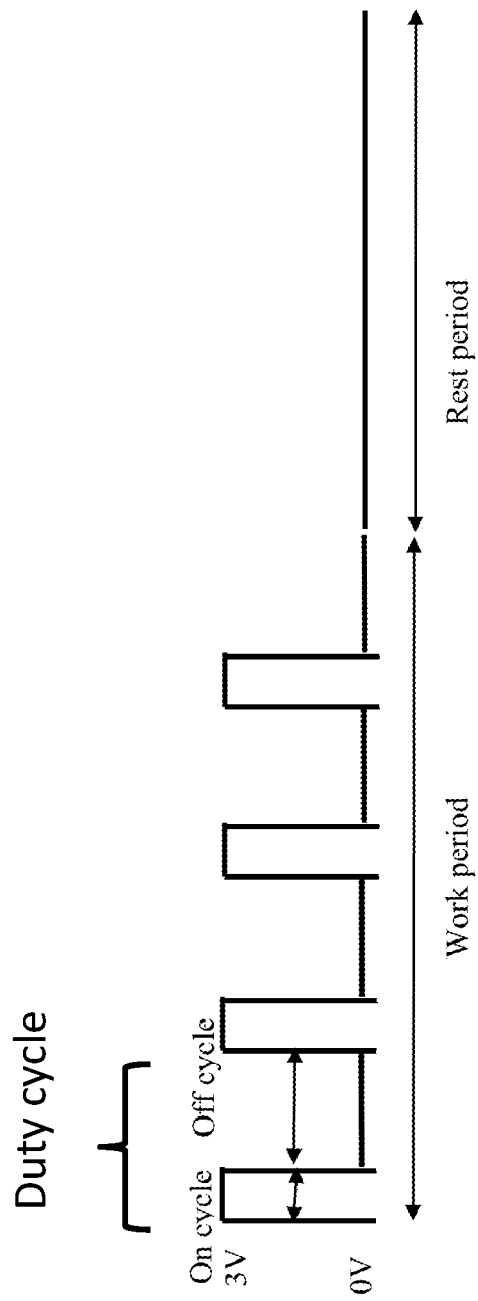
FIG. 6 diagrammatically illustrates a work cycle and duty cycle of an exemplary vibration capsule device in accordance with aspects of the present invention.
Figure 7:
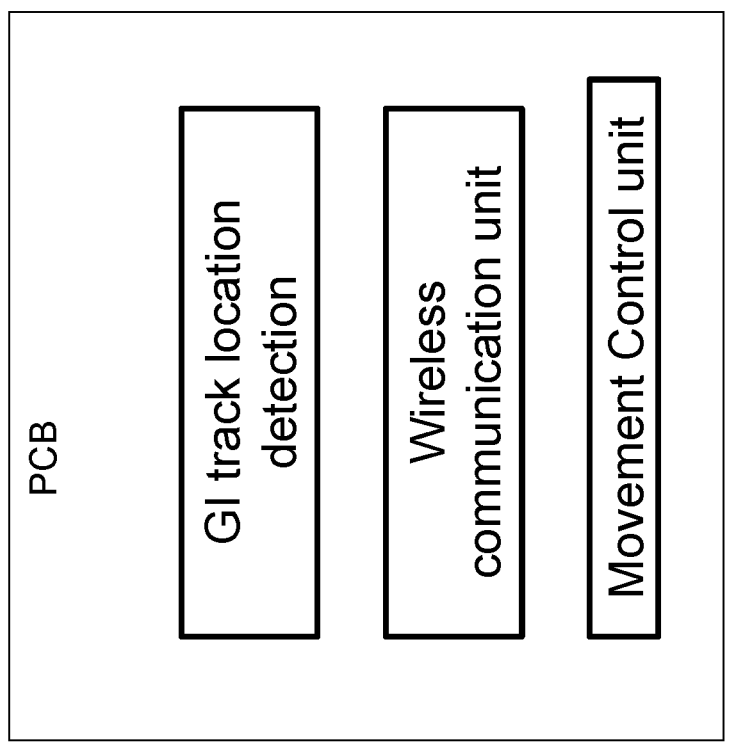
FIG. 7 schematically illustrate structural components for an exemplary PCB of the vibration capsule device in accordance with aspects of the present invention.

FIG. 3 shows an alternative embodiment of the vibration capsule device. The vibration capsule device comprises a movement generation unit, capable to generate vibration movement, characterized by a frequency between 1-20 Hz, duty cycle between 0.01 to 0.9 (FIG. 6); a movement control unit, configured to receive movement control signals from a wireless communication unit and a power management unit and send operable movement control instructions to the movement generation unit; and a power supply unit, providing power to the vibration capsule device through a power management unit, wherein the wireless communication unit comprises a RF transceiver and communicate data to an external device and receive instructions from the external device and wherein the power supply unit decides work period and rest period of the vibration capsule device (FIG. 6). Further the vibration capsule device comprises a capsule movement detection unit, which detects the vibration related parameters and sends to wireless communication unit.

Figure 4:
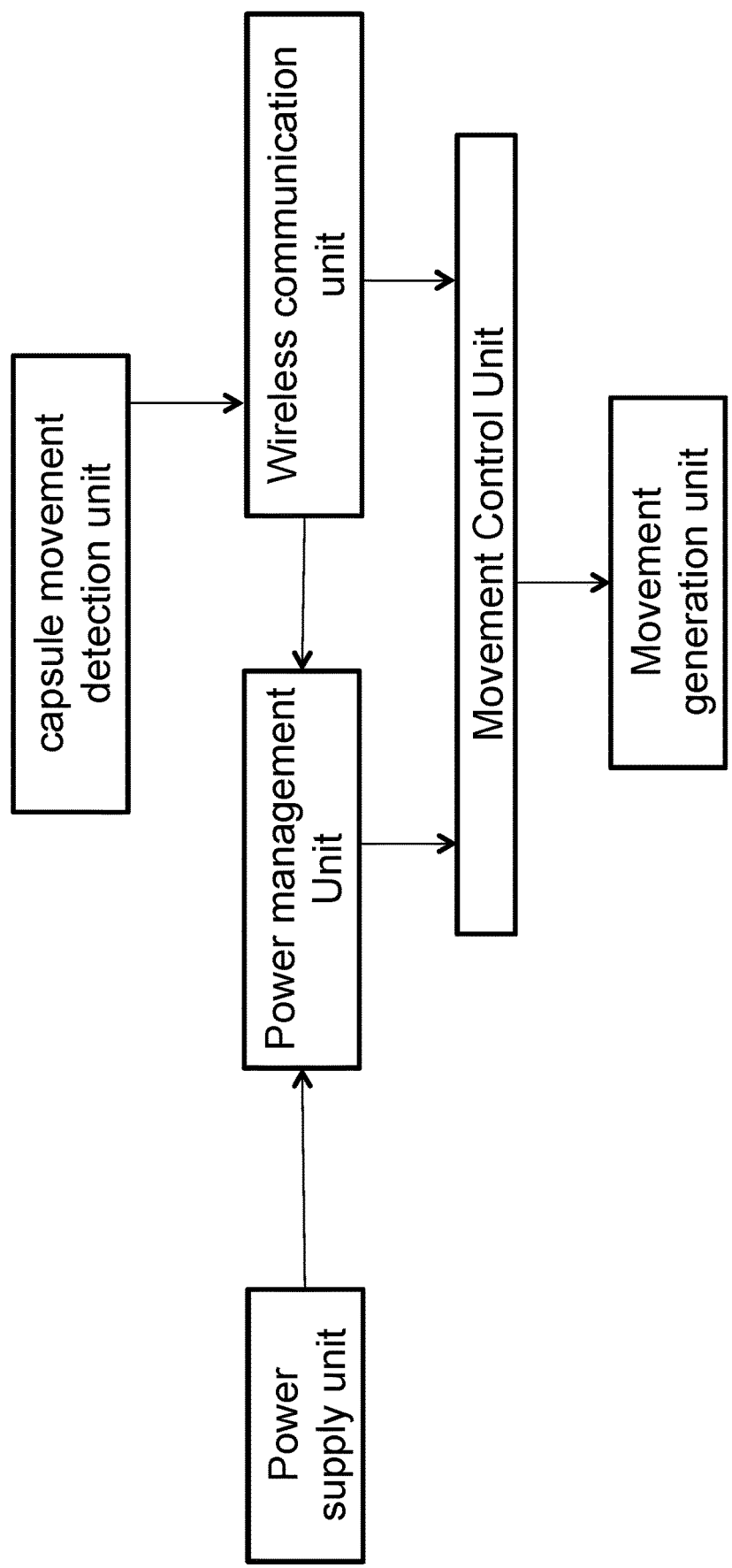
Figure 5:
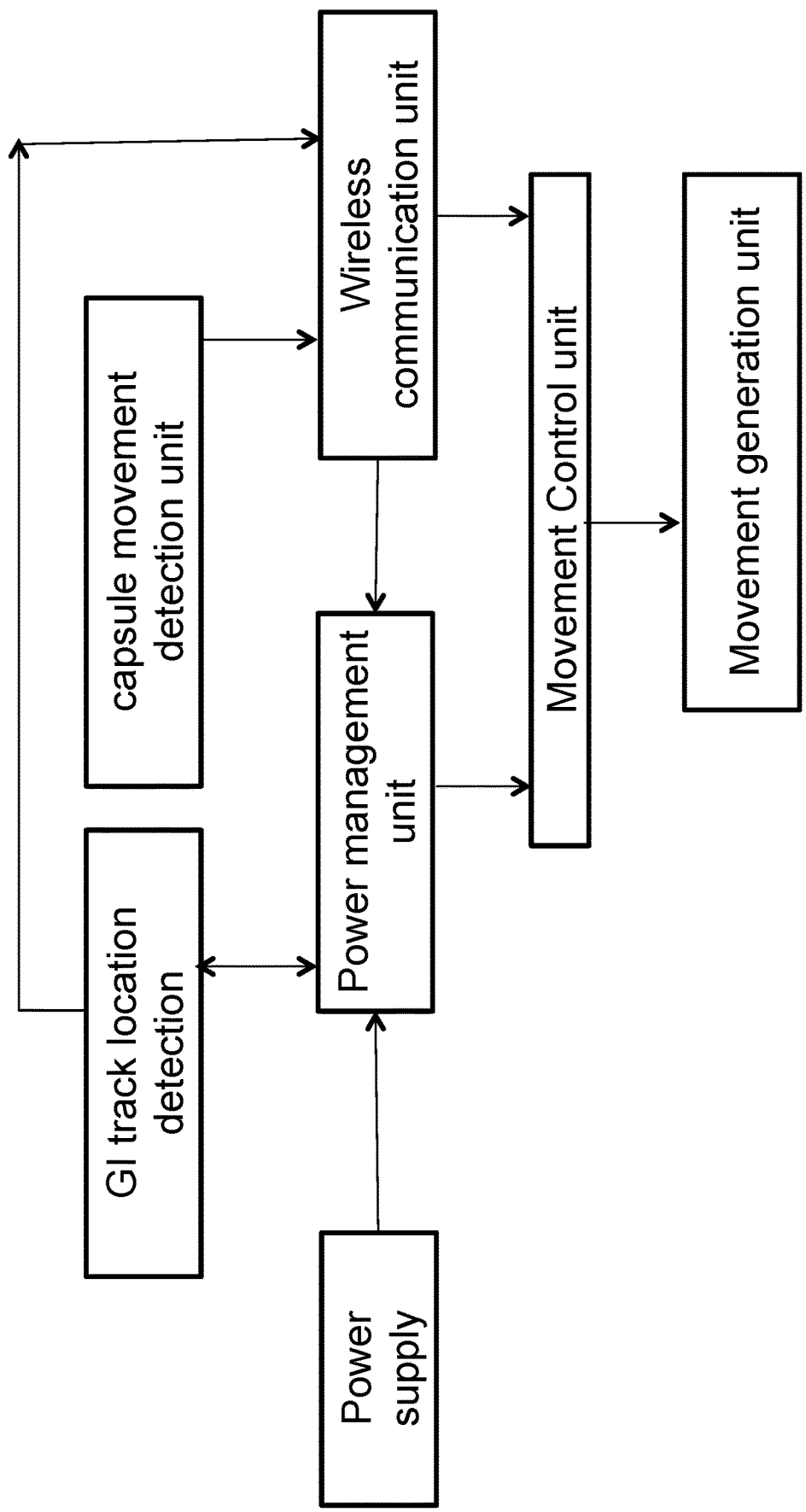
FIG. 5 diagrammatically illustrates functional units of another exemplary vibration capsule device having a GI tract location detection unit in accordance with aspects of the present invention.
Figure 8:
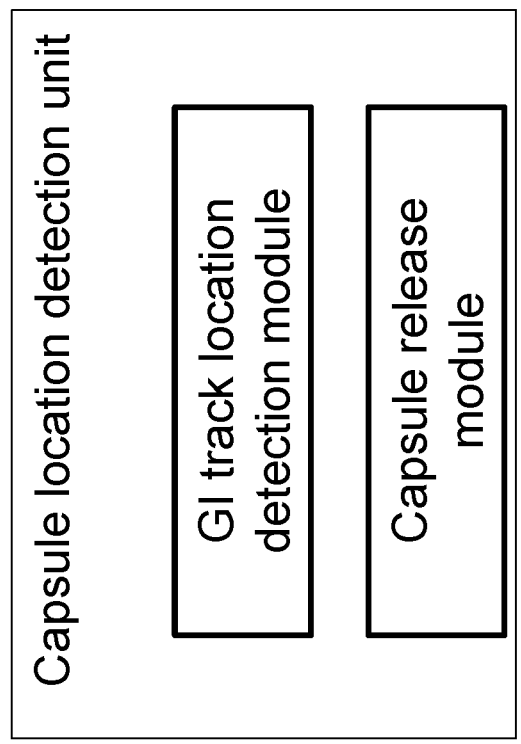
FIG. 8 schematically illustrate structural components for an exemplary capsule location detection unit of the vibration capsule device in accordance with aspects of the present invention.

Referring to FIG. 4, the vibration capsule device further comprises a GI tract location detection unit. The GI tract location detection unit detects the current location information of the vibration capsule device and send the current location information to the power management unit. Additionally, the GI tract location detection unit sends the current location information to the wireless communication unit. Referring to FIG. 8, capsule GI tract location detection unit comprise a GI tract position module and capsule release indication module.

Figure 10:
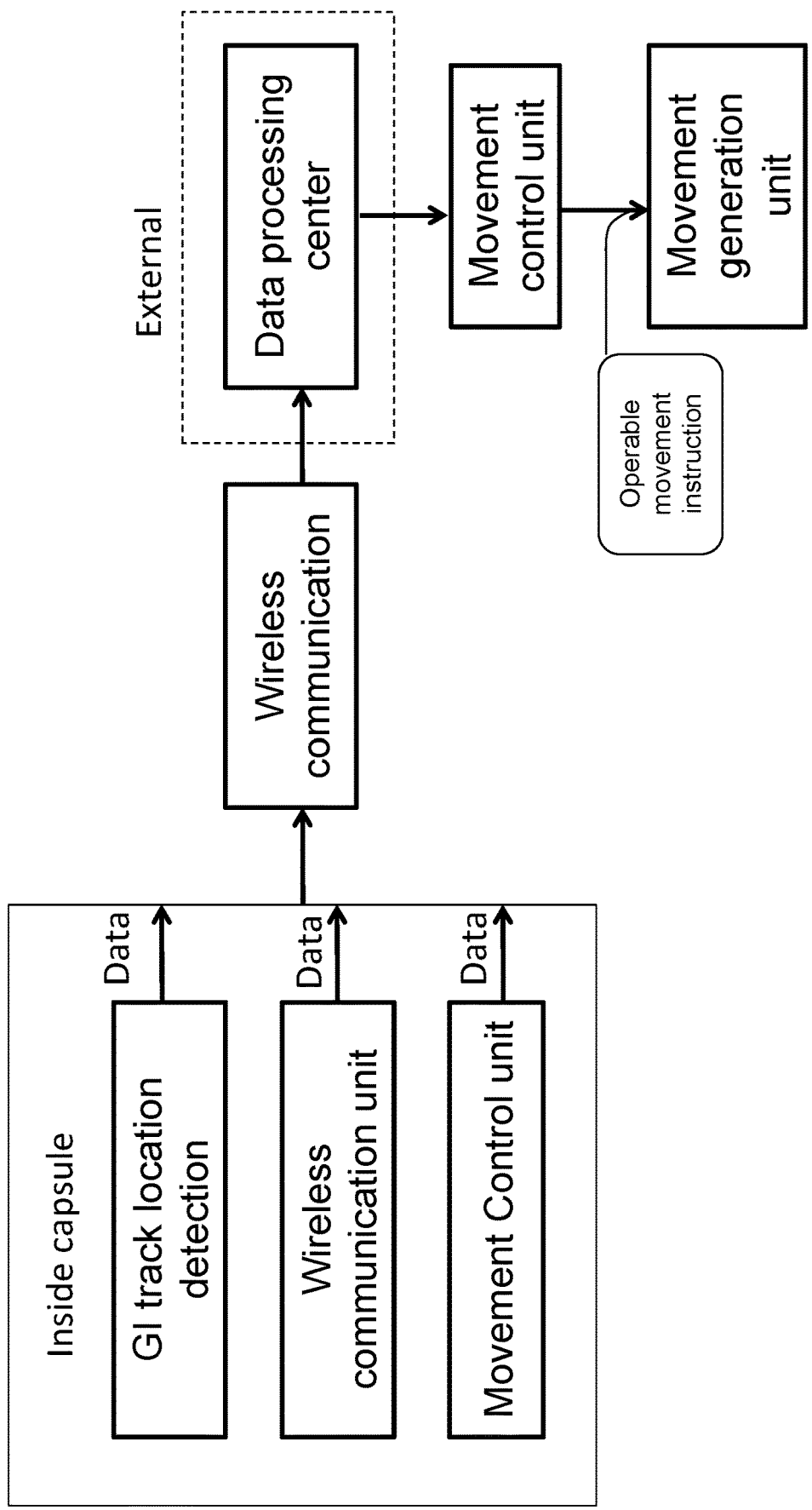
FIG. 10 shows in another embodiment how unprocessed data flows from capsule GI tract location detection unit, movement detection unit and wireless communication unit to the external unit, and then instruction flow into the movement generation unit.

Referring to FIG. 10, wireless communication unit can take input data from GI tract location detection unit and movement detection unit and send the data to an external device which may further connect to an external data center. The input data sent to wireless communication unit can be either raw data regarding the location and movement related parameters, or a processed data. The processed data can be an average, mean or maximum data for group of data collected.

Figure 11:
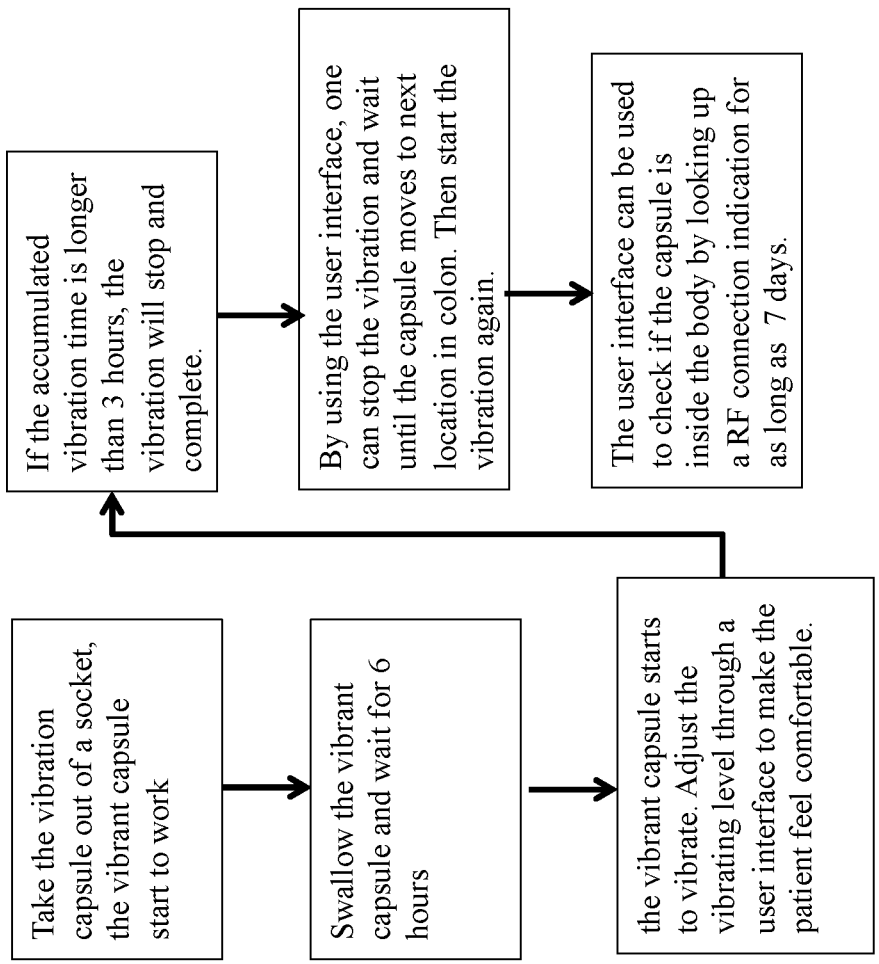
FIGS. 11 and 12 are flow diagrams of the method of using the vibration capsule device, in accordance with the aspects of the present invention.

FIG. 11 illustrate exemplary method of using of the vibration capsule device in accordance with the aspects of the present invention. The method includes taking the vibration capsule device out from a packaging socket turning the vibration capsule on; introducing the vibration capsule in to a stomach of a patient and waiting for 6 hours; performing a first vibration of the capsule, wherein the first vibrate is to move in a first vibration level having a first frequency and a first duty cycle, and each duty comprises a work period and rest period; adjusting the frequency level of through a user interface on an external device until the patient is comfortable; stop the vibration if the total accumulated work period is more than 3 hours. The method step further comprises turning on the GI tract detection unit, performing a second vibration when the capsule arrives at colon; deciding if the capsule is release by monitoring the position of the capsule using a RF monitor up to 7 days.

The method step of taking the vibration capsule device out from a packaging and turning the vibration capsule on further comprising a step of running a testing protocol on the vibration capsule device to confirm there is no malfunction of the vibration capsule device. The test protocol includes running the vibration device at a test frequency, at a test duty cycle for a pre-determined test period.

In the aforementioned method of using the vibration capsule device, before the step of performing the first vibration of the capsule, it further includes a step of receiving a default portfolio of vibration parameters by the vibration capsule device wirelessly. The capsule device receives the vibration parameters through a RF module and the default portfolio of vibration parameters include, but are not limited to, a first motor rotation speed, a first frequency, a first duty cycle, a first time duration or ratio between work period and rest period, a first movement direction and etc. In one example, the default portfolio of vibration parameters is associated with the vibration capsule device. In another example, the default portfolio of vibration parameters is specific to a patient and is determined by the patient's previous treatment history.

In another aspect of the method of using to the vibration capsule device of the present invention, the method comprises moving the vibration capsule device at a frequency synchronized with the motility of a GI tract of a patient. In another words, after introducing the vibration capsule device into a patient's GI tract, the capsule device vibrates at a frequency so that the capsule resonant with the internal organ of the patient, to achieve most efficacy and comfort.

In order to move the capsule device in vivo at a frequency resonate with an organ that it travels within; a method comprises the following steps:
a) starting a capsule movement unit at a first frequency f and a first duty cycle and detecting a first acceleration $A_f$ through a first acceleration sensor; b) vibrating the capsule movement unit at a second frequency f-m and at the first duty cycle, and detecting a second acceleration $A_{f-m}$ through the first acceleration sensor; and c) repeating steps b and c in the range from 1 Hz to 13 Hz and finding the maximum $A_{f-n}$. Then the f-n is resonant frequency of GI tract of a patient. wherein 1 Hz<f-m<13 Hz, 1 Hz<f-n<13 Hz and 0.2|m|<1.

In one example, the method includes a) starting the capsule movement unit at a first frequency f, wherein f is about 10 Hz and a first duty cycle and detecting a first acceleration $A_f$ through a first acceleration sensor; b) Then vibrating the capsule movement unit at a second frequency f-m at 9.5 Hz, wherein m=0.5 and at the first duty cycle, and c) detecting a second acceleration $A_{f-m}$ through the first acceleration sensor and recording the frequency value associated with a greater value between $A_f$ and $A_{f-m}$; and repeating steps b and c until the last frequency is 1 Hz and recording frequency associated with a maximum acceleration. Then the resulted frequency is the resonate frequency of the environment organ that the capsule is in.

Figure 12:
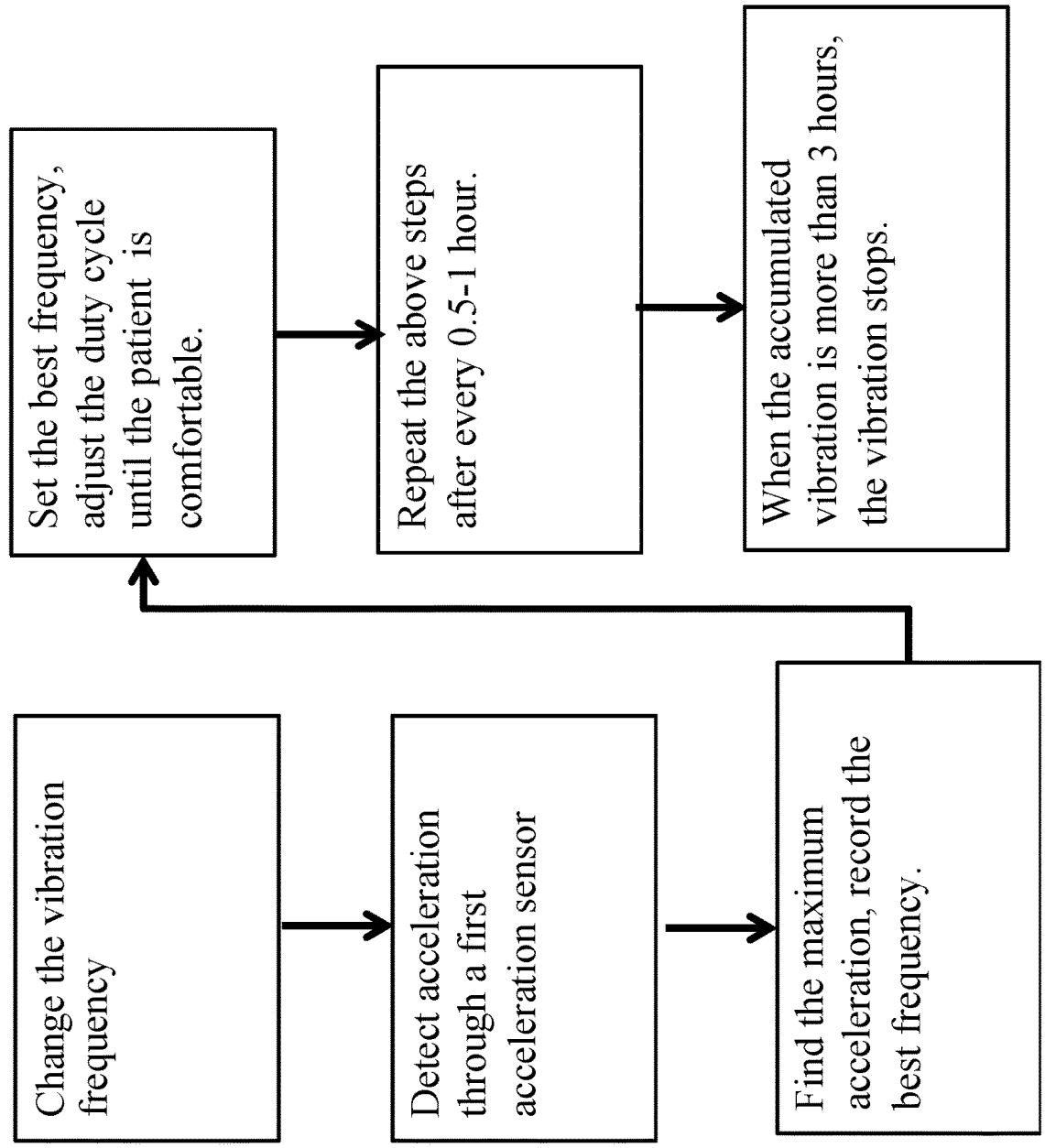

It is one object of the present invention to let the vibration capsule operate at an optimal vibration level for each patient, and the patient can experience most comfort without any discomfort while achieving a superior clinical goal. In one embodiment, referring to FIG. 12, the process includes starting the capsule movement unit at a third frequency and a third duty cycle; detecting a third acceleration through a first acceleration sensor; collecting at least three acceleration through the first sensor and forming a first group of data; identifying a maximum acceleration among the first group and recording the maximum acceleration as a first best frequency; adjusting the duty cycle until the patient is comfortable with the vibration level; repeating the detecting and adjusting step for every 0.5-1 hour and stop the vibration when the accumulated vibration is more than 3 hours.

It will be appreciated by those skilled in there art that the above discussion is for demonstration purpose; and the examples discussed above are some of many possible examples. Other variations are also applicable.

Any reference in this specification to "one embodiment," "an embodiment," "example embodiment," etc., means that a particular feature, structure, or characteristic described in connection with the embodiment is included in at least one embodiment of the invention. The appearances of such phrases in various places in the specification are not necessarily all referring to the same embodiment. Further, when a particular feature, structure, or characteristic is described in connection with any embodiment, it is submitted that it is within the purview of one skilled in the art to affect such feature, structure, or characteristic in connection with other ones of the embodiments. Furthermore, for ease of understanding, certain method procedures may have been delineated as separate procedures; however, these separately delineated procedures should not be construed as necessarily order dependent in their performance. That is, some procedures may be able to be performed in an alternative ordering, simultaneously, etc. In addition, exemplary diagrams illustrate various methods in accordance with embodiments of the present disclosure. Such exemplary method embodiments are described herein using and can be applied to corresponding apparatus embodiments, however, the method embodiments are not intended to be limited thereby.

Although few embodiments of the present invention have been illustrated and described, it would be appreciated by those skilled in the art that changes may be made in these embodiments without departing from the principles and spirit of the invention. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein. As used in this disclosure, the term "preferably" is non-exclusive and means "preferably, but not limited to." Terms in the claims should be given their broadest interpretation consistent with the general inventive concept as set forth in this description. For example, the terms "coupled" and "connect" (and derivations thereof) are used to connote both direct and indirect connections/couplings. As another example, "having" and "including", derivatives thereof and similar transitional terms or phrases are used synonymously with "comprising" (i.e., all are considered "open ended" terms)—only the phrases "consisting of" and "consisting essentially of" should be considered as "close ended". Claims are not intended to be interpreted under 112 sixth paragraph unless the phrase "means for" and an associated function appear in a claim and the claim fails to recite sufficient structure to perform such function.

We claim:

1. A vibration capsule device, comprising
a movement generation unit, providing an internal drive to produce a vibration for the vibration capsule device, at a first frequency and a first duty cycle;
a movement control unit, sending operable instructions to the movement generation unit to vibrate the vibration capsule device at the first frequency and the first duty cycle;
a power supply to provide power to the movement control unit and movement generation unit; and
a capsule movement detection unit including a plurality of sensors disposed at different parts of the vibration capsule device, and configured to detect and monitor vibration of the different parts of the vibration capsule device in real time, the plurality of sensors comprise an accelerometer, pressure sensor, temperature sensor, and magnetic field sensor configured to detect and monitor vibration related parameters from different parts of the vibration capsule device, including acceleration measurement, temperature measurement, pressure measurement, and ground magnetic field measurement, wherein the acceleration, temperature, pressure, and ground magnetic field measurements are configured to provide quantitative feedback regarding a vibration level of the vibration capsule device;
a wireless communication unit, which sends out capsule movement data, detected by the capsule movement detection unit, which comprises the vibration related parameters from different parts of the vibration capsule device, including acceleration, temperature, pressure and ground magnetic field, to an external device and receives feedback from the external device to change or maintain vibration parameters, and
wherein the vibration related parameters are configured to provide vibration profile in real time to a patient; a capsule gastrointestinal (GI) tract location detection unit configured to detect a current location of the vibration device and send data of the current location of the vibration capsule device that was detected to either the wireless communication unit or the movement control unit, and wherein the vibration level is further adjusted based on the data of the current location of the capsule device that was detected by the capsule GI tract location detection unit.

2. The vibration capsule device of claim 1, wherein the movement generation unit is selected from a button eccentric motor, a linear eccentric motor, and a magnetic eccentric module.

3. The vibration capsule device of claim 1, wherein the movement generation unit comprises a motor and the motor is disposed along a capsule axis and when the capsule device vibrates, a vibration direction is perpendicular to the capsule axis of the capsule device.

4. The vibration capsule device of claim 3, wherein the motor in the movement generation unit is configured to rotate between 100 cycles/min and 10000 cycles/min.

5. The vibration capsule device of claim 1, wherein the first frequency is between 1-20 Hertz (Hz).

6. The vibration capsule device of claim 1, wherein the first duty cycle is adjustable between 0.01 to 0.9.

7. The vibration capsule device of claim 1, wherein the operable instructions are to increase, decrease or maintain the vibration parameters including motor rotation speed and ratio between work period and rest period.

8. The vibration capsule device of claim 1, wherein the plurality of sensors further comprise a gyro sensor.

9. The vibration capsule device of claim 1, wherein the capsule GI tract location detection unit including a position detection unit and capsule release indication unit.

10. The vibration capsule device of claim 9, wherein the capsule movement data further includes at least one data from the capsule GI tract location detection unit.

11. The vibration capsule device of claim 1, wherein the capsule GI tract location detection unit employs one of the methods selected from a time-delay calculation method, a PH-measurement method, a small magnet tracing method, a radio frequency (RF) positioning method and an enzyme triggering method.

12. The vibration capsule device of claim 1, further comprises a capsule ON and OFF module, selected from a magnetic reed switch, a photosensitive irradiation switch, an alternating current (AC) magnetic field sensor switch, a radio frequency (RF) sensor switch, and a temperature sensor switch.

13. The vibration capsule device of claim 1, wherein the wireless communication unit is one selected from a radio frequency (RF) communication means, alternating current (AC) magnetic field interactive means, and in body contact electrode.

14. The vibration capsule device of claim 1, wherein the wireless communication unit includes radio frequency (RF) antennas, a radio frequency (RF) transceiver module and a printed circuit board (PCB) unit.

15. The vibration capsule device of claim 14, wherein the radio frequency (RF) transceiver module is configured to use either 433 Megahertz (MHz), or 2.4 Gigahertz (GHz).

16. The vibration capsule device of claim 1, wherein the external device is a smart phone.

* * * * *